(12) United States Patent
Weber et al.

(10) Patent No.: US 11,559,394 B2
(45) Date of Patent: *Jan. 24, 2023

(54) PROSTHETIC VALVES, VALVE LEAFLETS AND RELATED METHODS

(71) Applicant: Boston Scientific Scimed, Inc., Maple Grove, MN (US)

(72) Inventors: Jan Weber, Maastricht (NL); Haiying Zhou, Plymouth, MN (US); Bruce R. Forsyth, Hanover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 601 days.

This patent is subject to a terminal disclaimer.

(21) Appl. No.: 16/526,150

(22) Filed: Jul. 30, 2019

(65) Prior Publication Data
US 2019/0350703 A1 Nov. 21, 2019

Related U.S. Application Data

(63) Continuation of application No. 15/595,176, filed on May 15, 2017, now Pat. No. 10,368,982.

(Continued)

(51) Int. Cl.
*A61F 2/24* (2006.01)
*A61L 27/14* (2006.01)
(Continued)

(52) U.S. Cl.
CPC ............ *A61F 2/2412* (2013.01); *A61L 27/14* (2013.01); *A61L 27/306* (2013.01); *B32B 27/02* (2013.01);
(Continued)

(58) Field of Classification Search
None
See application file for complete search history.

(56) References Cited

U.S. PATENT DOCUMENTS 4,016,714 A 4/1977 Crandall
4,340,091 A 7/1982 Davis et al.
(Continued)

FOREIGN PATENT DOCUMENTS

CN 1449266 10/2003
CN 1621424 6/2005
(Continued)

OTHER PUBLICATIONS

Communication Pursuant to Article 94(3) EPC for European Patent Application No. 16715218.0 dated Feb. 14, 2020 (6 pages).
(Continued)

*Primary Examiner* — Rebecca S Preston
(74) *Attorney, Agent, or Firm* — Pauly, DeVries Smith & Deffner LLC

(57) ABSTRACT

Examples herein include prosthetic valves, valve leaflets and related methods. In an example, a prosthetic valve is included having a plurality of leaflets. The leaflets can each have a root portion and an edge portion substantially opposite the root portion and movable relative to the root portion. The leaflets can include a fibrous matrix including polymeric fibers having an average diameter of about 10 nanometers to about 10 micrometers. A coating can surround the polymeric fibers within the fibrous matrix. The coating can have a thickness of about 3 to about 30 nanometers. The coating can be formed of a material selected from the group consisting of a metal oxide, a nitride, a carbide, a sulfide, or fluoride. In an example, a method of making a valve is included. Other examples are also included herein.

19 Claims, 7 Drawing Sheets

Related U.S. Application Data

(60) Provisional application No. 62/338,722, filed on May 19, 2016.

(51) Int. Cl.

| | | |
|---|---|---|
| *A61L 27/30* | (2006.01) | |
| *D04H 1/541* | (2012.01) | |
| *B32B 27/02* | (2006.01) | |
| *C08K 3/22* | (2006.01) | |
| *D01F 8/00* | (2006.01) | |
| *D04H 3/147* | (2012.01) | |

(52) U.S. Cl.
CPC ............ *C08K 3/22* (2013.01); *D04H 1/5412* (2020.05); *A61F 2/2415* (2013.01); *A61F 2/2418* (2013.01); *A61F 2210/0076* (2013.01); *A61F 2250/0017* (2013.01); *A61F 2250/0023* (2013.01); *A61F 2250/0028* (2013.01); *A61F 2250/0036* (2013.01); *A61F 2250/0076* (2013.01); *C08K 2003/2227* (2013.01); *C08K 2003/2241* (2013.01); *C08K 2003/2255* (2013.01); *D01F 8/00* (2013.01); *D04H 3/147* (2013.01)

(56) References Cited

U.S. PATENT DOCUMENTS

| | | | |
|---|---|---|---|
| 4,731,074 | A | 3/1988 | Rousseau et al. |
| 4,753,652 | A | 6/1988 | Langer et al. |
| 4,778,461 | A | 10/1988 | Pietsch et al. |
| 5,296,292 | A | 3/1994 | Butters |
| 5,476,507 | A | 12/1995 | Wakabayashi et al. |
| 5,674,286 | A | 10/1997 | D'alessio et al. |
| 5,679,299 | A | 10/1997 | Gilbert et al. |
| 5,688,597 | A | 11/1997 | Kohno |
| 5,740,051 | A | 4/1998 | Sanders, Jr. et al. |
| 5,843,158 | A | 12/1998 | Lenker et al. |
| 6,165,215 | A | 12/2000 | Rettenberg et al. |
| 6,726,715 | B2 | 4/2004 | Sutherland |
| 6,953,332 | B1 | 10/2005 | Kurk et al. |
| 7,335,264 | B2 | 2/2008 | Austin et al. |
| 7,517,353 | B2 | 4/2009 | Weber |
| 7,521,296 | B2 | 4/2009 | Wood et al. |
| 7,615,335 | B2 | 11/2009 | Shelnut et al. |
| 7,786,670 | B2 | 8/2010 | Veres et al. |
| 7,988,900 | B2 | 8/2011 | Beith et al. |
| 8,043,551 | B2 | 10/2011 | Heim et al. |
| 8,324,290 | B2 | 12/2012 | Desai et al. |
| 8,361,144 | B2 | 1/2013 | Fish et al. |
| 8,529,934 | B2 | 9/2013 | Desai et al. |
| 8,590,747 | B2 | 11/2013 | Keller et al. |
| 8,845,580 | B2 | 9/2014 | Gellman et al. |
| 8,864,816 | B2 | 10/2014 | Flanagan et al. |
| 8,945,212 | B2 | 2/2015 | Bruchman et al. |
| 8,975,372 | B2 | 3/2015 | Ju et al. |
| 9,056,006 | B2 | 6/2015 | Edelman et al. |
| 9,074,318 | B2 | 7/2015 | Chou et al. |
| 9,145,627 | B2 | 9/2015 | Wilson et al. |
| 9,205,172 | B2 | 12/2015 | Neethling et al. |
| 9,255,929 | B2 | 2/2016 | Jiang et al. |
| 9,481,949 | B2 | 11/2016 | Zhang et al. |
| 9,554,900 | B2 | 1/2017 | Bruchman et al. |
| 9,737,400 | B2 | 8/2017 | Fish et al. |
| 9,814,572 | B2 | 11/2017 | Edelman et al. |
| 9,944,529 | B2 | 4/2018 | Zhang et al. |
| 9,987,130 | B2 | 6/2018 | Weber |
| 10,195,023 | B2 | 2/2019 | Wrobel |
| 10,299,915 | B2 | 5/2019 | Edelman et al. |
| 10,314,696 | B2 | 6/2019 | Wulfman et al. |
| 10,368,982 | B2 * | 8/2019 | Weber .................. D04H 1/5412 |
| 10,413,403 | B2 | 9/2019 | Boden et al. |
| 10,433,955 | B2 | 10/2019 | Edelman et al. |
| 10,716,671 | B2 | 7/2020 | Eppihimer et al. |
| 10,874,843 | B2 | 12/2020 | Adenusi et al. |
| 10,925,998 | B2 | 2/2021 | Delaney, Jr. et al. |
| 11,304,798 | B2 | 4/2022 | Wulfman |
| 2001/0025196 | A1 | 9/2001 | Chinn et al. |
| 2002/0082689 | A1 | 6/2002 | Chinn et al. |
| 2003/0055496 | A1 | 3/2003 | Cai et al. |
| 2003/0078652 | A1 | 4/2003 | Sutherland et al. |
| 2003/0097175 | A1 | 5/2003 | O'connor et al. |
| 2003/0171802 | A1 | 9/2003 | Wilder et al. |
| 2003/0183982 | A1 | 10/2003 | Jansen et al. |
| 2004/0015233 | A1 | 1/2004 | Jansen et al. |
| 2004/0022939 | A1 | 2/2004 | Kim et al. |
| 2004/0088046 | A1 | 5/2004 | Speziali |
| 2004/0122515 | A1 | 6/2004 | Chu |
| 2005/0228486 | A1 | 10/2005 | Flagle et al. |
| 2005/0239508 | A1 | 10/2005 | Schwarz et al. |
| 2006/0171985 | A1 | 8/2006 | Richard et al. |
| 2006/0190074 | A1 | 8/2006 | Hill et al. |
| 2007/0118210 | A1 | 5/2007 | Pinchuk et al. |
| 2007/0144124 | A1 | 6/2007 | Schewe et al. |
| 2007/0232169 | A1 | 10/2007 | Strickler et al. |
| 2007/0254005 | A1 | 11/2007 | Pathak et al. |
| 2008/0045420 | A1 | 2/2008 | Karagianni et al. |
| 2009/0041978 | A1 | 2/2009 | Sogard et al. |
| 2009/0054969 | A1 | 2/2009 | Salahieh et al. |
| 2009/0117334 | A1 | 5/2009 | Sogard et al. |
| 2009/0149673 | A1 | 6/2009 | Zhang et al. |
| 2009/0155335 | A1 | 6/2009 | Oshaughnessey et al. |
| 2009/0324679 | A1 | 12/2009 | Ippoliti et al. |
| 2010/0023104 | A1 | 1/2010 | Desai et al. |
| 2010/0179298 | A1 | 7/2010 | Faust et al. |
| 2010/0249922 | A1 | 9/2010 | Li et al. |
| 2011/0022160 | A1 | 1/2011 | Flanagan et al. |
| 2011/0045030 | A1 | 2/2011 | Desai et al. |
| 2011/0208299 | A1 | 8/2011 | Marissen et al. |
| 2011/0305898 | A1 | 12/2011 | Zhang et al. |
| 2012/0101567 | A1 | 4/2012 | Jansen |
| 2012/0122359 | A1 | 5/2012 | Lee et al. |
| 2012/0172978 | A1 | 7/2012 | Dumontelle |
| 2012/0258313 | A1 | 10/2012 | Wen et al. |
| 2012/0290082 | A1 | 11/2012 | Quint et al. |
| 2013/0150957 | A1 | 6/2013 | Weber et al. |
| 2013/0211508 | A1 | 8/2013 | Lane et al. |
| 2013/0274874 | A1 | 10/2013 | Hammer et al. |
| 2014/0005771 | A1 | 1/2014 | Braido et al. |
| 2014/0005772 | A1 | 1/2014 | Edelman et al. |
| 2014/0018440 | A1 | 1/2014 | Boden et al. |
| 2014/0088716 | A1 | 3/2014 | Zubok et al. |
| 2014/0163671 | A1 | 6/2014 | Bruchman et al. |
| 2014/0180402 | A1 | 6/2014 | Bruchman et al. |
| 2014/0322512 | A1 * | 10/2014 | Pham .................. D01F 8/16 428/220 |
| 2015/0005869 | A1 | 1/2015 | Soletti et al. |
| 2015/0182332 | A1 | 7/2015 | Edelman et al. |
| 2015/0265392 | A1 | 9/2015 | Flanagan et al. |
| 2016/0296322 | A1 | 10/2016 | Edelman |
| 2016/0296323 | A1 | 10/2016 | Wulfman et al. |
| 2016/0296325 | A1 | 10/2016 | Edelman |
| 2016/0354201 | A1 | 12/2016 | Keogh |
| 2017/0000610 | A1 | 1/2017 | Eppihimer et al. |
| 2017/0014227 | A1 | 1/2017 | Boden et al. |
| 2017/0071729 | A1 | 3/2017 | Wrobel |
| 2017/0156854 | A1 | 6/2017 | Hammer |
| 2017/0231758 | A1 | 8/2017 | Bruchman et al. |
| 2017/0266350 | A1 | 9/2017 | Jiang et al. |
| 2017/0333185 | A1 | 11/2017 | Weber et al. |
| 2018/0049869 | A1 | 2/2018 | Edelman et al. |
| 2018/0206982 | A1 | 7/2018 | Haivatov et al. |
| 2018/0303972 | A1 | 10/2018 | Delaney, Jr. et al. |
| 2019/0262131 | A1 | 8/2019 | Wulfman et al. |
| 2021/0154006 | A1 | 5/2021 | Humair et al. |
| 2021/0170069 | A1 | 6/2021 | Delaney, Jr. et al. |

FOREIGN PATENT DOCUMENTS

| | | |
|---|---|---|
| CN | 1874799 | 12/2006 |
| CN | 101437663 | 5/2009 |
| CN | 101505723 | 8/2009 |
| CN | 101690683 | 4/2010 |
| CN | 102602083 | 7/2012 |

(56) References Cited

FOREIGN PATENT DOCUMENTS

| | | |
|---|---|---|
| CN | 103628147 | 3/2014 |
| CN | 104203151 | 12/2014 |
| CN | 104220104 | 12/2014 |
| CN | 104674578 | 6/2015 |
| CN | 104780952 | 7/2015 |
| CN | 106084094 | 11/2016 |
| CN | 107405426 | 11/2017 |
| CN | 107427366 | 12/2017 |
| CN | 107735052 | 2/2018 |
| CN | 107847321 | 3/2018 |
| CN | 108024857 | 5/2018 |
| CN | 109475409 | 3/2019 |
| EP | 0331345 | 9/1989 |
| EP | 3280357 | 2/2018 |
| EP | 3280358 | 2/2018 |
| EP | 3322382 | 5/2018 |
| EP | 3349693 | 7/2018 |
| EP | 2866847 | 8/2018 |
| EP | 3457989 | 3/2019 |
| EP | 3316818 | 5/2019 |
| JP | S54090897 | 7/1979 |
| JP | S58133318 | 9/1983 |
| JP | H0654868 | 3/1994 |
| JP | 2013144009 | 7/2013 |
| JP | 2018516610 | 6/2018 |
| JP | 2018516617 | 6/2018 |
| JP | 2018521765 | 8/2018 |
| JP | 2018523503 | 8/2018 |
| JP | 2018527098 | 9/2018 |
| WO | 0224119 | 3/2002 |
| WO | 02074201 | 9/2002 |
| WO | 2004080346 | 2/2005 |
| WO | 2005039664 | 5/2005 |
| WO | 2006000763 | 1/2006 |
| WO | 2008097592 | 8/2008 |
| WO | 2009038761 | 3/2009 |
| WO | 2010020660 | 2/2010 |
| WO | 2010048281 | 4/2010 |
| WO | 2014008207 | 1/2014 |
| WO | 2014143866 | 9/2014 |
| WO | 2014149319 | 9/2014 |
| WO | 2014158444 | 10/2014 |
| WO | 2014163795 | 10/2014 |
| WO | 2016025945 | 2/2016 |
| WO | 2016164197 | 10/2016 |
| WO | 2016164209 | 10/2016 |
| WO | 2017004035 | 1/2017 |
| WO | 2017011392 | 1/2017 |
| WO | 2017048575 | 3/2017 |
| WO | 2017200920 | 11/2017 |
| WO | 2018200378 | 11/2018 |
| WO | 2019210059 | 10/2019 |

OTHER PUBLICATIONS

First Examination Report for Australian Patent Application No. 2016285561 dated Mar. 12, 2020 (3 pages).
First Office Action for Chinese Patent Application No. 201680018663.3 dated Mar. 16, 2020 (12 pages) with English Summary.
Non-Final Office Action for U.S. Appl. No. 15/959,894 dated May 5, 2020 (63 pages).
Notice of Allowance for U.S. Appl. No. 15/193,794 dated Mar. 16, 2020 (12 pages).
Office Action for Japanese Patent Application No. 2017-549776 dated Dec. 17, 2019 (9 pages) with English Translation.
Office Action for Japanese Patent Application No. 2017552443 dated Dec. 17, 2019 (14 pages) with English Translation.
Office Action for Japanese Patent Application No. 2017-564627 dated Jan. 21, 2020 (9 pages) with English Translation.
Response to Non-Final Rejection dated Dec. 6, 2019 for U.S. Appl. No. 15/193,794, submitted via EFS-Web filed Mar. 4, 2020, 4 pages.
Third Office Action for Chinese Patent Application No. 201680036250.8 dated Mar. 2, 2020 (10 pages) with English Summary.

Third Office Action for Chinese Patent Application No. 201680018700.0 dated Feb. 3, 2020 (6 pages) No English Translation.
"Communication Pursuant to Article 94(3) EPC," for European Patent Application No. 16715724.7 dated Apr. 15, 2021 (4 pages).
"First Office Action," for Chinese Patent Application No. 201880024683.0 dated May 28, 2021 (11 pages) with English Summary.
"Non-Final Office Action," for U.S. Appl. No. 16/413,104 dated Jul. 20, 2021 (74 pages).
"Office Action," for Japanese Patent Application No. 2018-501287 dated Jun. 15, 2021 (4 pages).
"Response to Communication Pursuant to Article 94(3) EPC," for European Patent Application No. 16715724.7 filed Aug. 9, 2021 (53 pages).
Decision of Rejection for Chinese Patent Application No. 201380044842.0 dated Sep. 17, 2019 (6 pages) No English Translation.
International Preliminary Report on Patentability for PCT Application No. PCT/US2018/028864 dated Nov. 7, 2019 (7 pages).
Non-Final Office Action for U.S. Appl. No. 15/193,794 dated Dec. 6, 2019 (8 pages).
Second Office Action for Chinese Patent Application No. 201680040898.2 dated Nov. 4, 2019 (10 pages), no English translation.
Aksoy, Ayse E. et al., "Surface Modification of Polyurethanes with Covalent Immobilization of Heparin," Macromolecular Symposia, vol. 269, Issue 1, pp. 145-153, Aug. 2008 (9 pages).
Alferiev, Ivan et al., "Prevention of polyurethane valve cusp calcification with covalently attached bisphosphonate diethylamino moieties," J Biomed Mater Res 66A: 385-395, 2003 (11 pages).
Athappan, Ganesh et al., "Influence of Transcatheter Aortic Valve Replacement Strategy and Valve Design on Stroke After Transcatheter Aortic Valve Replacement: A Meta-Analysis and Systematic Review of Literature," J Am Coll Cardiol. 2014;63(20):2101-2110 (10 pages).
Barkoula, Nektaria-Marianthi et al., "Processing of Single Polymer Composites Using the Concept of Constrained Fibers," Polymer Composites, 2005, 26: p. 114-120 (7 pages).
Bastiaansen, Cees W. et al., "Melting Behavior of Gelspun-Drawn Polyolefins," Makromol. Chem., Macromol. Symp., 1989. 28: p. 73-84 (12 pages).
Bates, Frank S. et al., "Multiblock Polymers: Panacea or Pandora's Box?," Science, 2012, 336:434-440 (7 pages).
Berkland, Cory et al., "Controlling surface nano-structure using flow-limited field-injection electrostatic spraying (FFESS) of poly(D,L-lactide-co-glycolide)," Biomaterials (2004) 25: 5649-5658 (10 pages).
Bernacca, Gillian M. et al., "Mechanical and morphological study of biostable polyurethane heart valve leaflets explanted from sheep," J Biomed Mater Res 61:138-145, 2002 (8 pages).
Bhattacharyya, D. et al., "Polyamide 6 single polymer composites," eXPRESS Polym. Lett., 2009. 3(8): p. 525-532 (8 pages).
Cacciola, G. et al., "A Synthetic Fiber-Reinforced Stentless Heart Valve," Journal of Biomechanics, Jan. 1, 2000, pp. 653-658, XP055284947, Retrieved from the Internet: URL:http://ac.els-cdn.com.
Cacciola, G. et al., "A Three-Dimesional Mechanical Analysis of a Stentless Fibre-Reinforced Aortic Valve Prosthesis," Journal of Biomechanics, Jan. 1, 2000, pp. 521-530, XP055284955, Retrieved from the Internet: URL:http://ac.els-cdn.com.
Charles, Lyndon F. et al., "Self-reinforced composites of hydroxyapatite-coated PLLA fibers: fabrication and mechanical characterization," J. Mech. Behav. Biomed. Mater., 2013. 17: p. 269-277 (9 pages).
Claiborne, Thomas E. et al., "In Vitro Evaluation of a Novel Hemodynamically Optimized Trileaflet Polymeric Prosthetic Heart Valve," Journal of Biomechanical Engineering 2013, vol. 135 (8 pages).
De Yoreo, James J. et al., "Principles of Crystal Nucleation and Growth," Biomineralization, Mineral Soc. Am., Washington, DC, 2003, pp. 57-93 (37 pages).
"Decision of Final Rejection," for China Patent Application No. 201380044842.0, dated Apr. 7, 2017 (18 pages) with Summary.

(56) References Cited

OTHER PUBLICATIONS

Dencheva, Nadya et al., "Structure-properties relationship in single polymer composites based on polyamide 6 prepared by in-mold anionic polymerization," J. Mater. Sci., 2013. 48(20): p. 7260-7273 (14 pages).
Duhovic, Miro P. et al., "Polyamide 66 polymorphic single polymer composites," Open Macromol. J., 2009. 3: p. 37-40. (4 pages).
Fabreguette, et al., "X-ray mirrors on flexible polymer substrates fabricated by atomic layer deposition," Thin Solid Films 515: 7177-7180 (2007), 5 pages.
Fabreguette, Francois H. et al., "Ultrahigh x-ray reflectivity from W/Al2O3 multilayers fabricated using atomic layer deposition," Applied Physics Letters 88:013166 (2006), 3 pages.
Fakirov, Stoyko "Nano- and Microfibrillar Single-Polymer Composites: A Review," Macromol. Mater. Eng., 2013. 298(1): p. 9-32 (24 pages).
Feng, Yakai et al., "Surface modification of polycarbonate urethane by covalent linkage of heparin with a PEG spacer," Transactions of Tianjin University, Feb. 2013, vol. 19, Issue 1, pp. 58-65 (8 pages).
File History for U.S. Appl. No. 14/656,044, filed Sep. 11, 2019 (372 pages).
File History for U.S. Appl. No. 15/797,394, filed Sep. 11, 2019 (287 pages).
File History for U.S. Appl. No. 15/082,239, filed Sep. 11, 2019 (319 pages).
File History for U.S. Appl. No. 15/205,098, filed Sep. 11, 2019 (260 pages).
File History for U.S. Appl. No. 15/257,211, filed Sep. 11, 2019 (224 pages).
File History for U.S. Appl. No. 15/595,176, filed Sep. 11, 2019 (238 pages).
File History for European Patent Application No. 13739321.1 downloaded Sep. 12, 2019 (377 pages).
File History for U.S. Appl. No. 13/932,968, filed Sep. 12, 2019 (360 pages).
File History for European Patent Application No. 16715218.0 downloaded Sep. 12, 2019 (162 pages).
File History for European Patent Application No. 1671524.7 downloaded Sep. 12, 2019 (251 pages).
File History for U.S. Appl. No. 16/413,104, filed Sep. 12, 2019 (129 pages).
File History for U.S. Appl. No. 15/082,382, filed Sep. 12, 2019 (264 pages).
File History for U.S. Appl. No. 15/082,293, filed Sep. 12, 2019 (229 pages).
File History for European Patent Application No. 16736720.0 downloaded Sep. 12, 2019 (255 pages).
File History for U.S. Appl. No. 15/193,794, filed Sep. 12, 2019 (369 pages).
File History for European Patent Application No. 16741492.9 downloaded Sep. 12, 2019 (217 pages).
File History for European Patent Application No. 16766455.6 downloaded Sep. 12, 2019 (249 pages).
File History for European Patent Application No. 17725140.2 downloaded Sep. 12, 2019 (119 pages).
"First Office Action," for Chinese Patent Application No. 201380044842.0 dated Dec. 18, 2015 (15 pages) with English Translation.
"First Office Action," for Chinese Patent Application No. 20160036250.8 dated Nov. 2, 2018 (11 pages) with English Summary.
"First Office Action," for Chinese Patent Application No. 201680018700.0 dated Nov. 2, 2018 (12 pages) with English Summary.
"First Office Action," for Chinese Patent Application No. 201680040898.2 dated Feb. 28, 2019, 17 pages, with English summary.
"First Office Action," for Chinese Patent Application No. 201680053293.7 dated Mar. 5, 2019 (5 pages) No English Translation.
Gallocher, "Durability Assessment of Polymer Trileaflet Heart Valves," FIU Electronic Theses and Dissertations, Paper 54, 2007 (237 pages).
Généreux, Philippe et al., "Vascular Complications After Transcatheter Aortic Valve Replacement: Insights from the PARTNER Trial," J Am Coll Cardiol. 2012;60(12):1043-1052 (10 pages).
George, "Final Report—Fabrication of Nanolaminates with Ultrathin Nanolayers Using Atomic Layer Deposition: Nucleation & Growth Issues," AFOSR Grant No. FA9550-01-1-0075 Feb. 2009 (36 pages).
"Glycosaminoglycan," Wikipedia, posted on or before Oct. 16, 2004, retrieved Feb. 13, 2014, http://en.wikipedia.org/wiki/Glycosaminoglycan, 6 pages.
Gong, Ying et al., "Polyamide single polymer composites prepared via in situ anionic polymerization of ε-caprolactam," Composites, Part A, 2010. 41A(8): p. 1006-1011 (6 pages).
Gong, Ying et al., "Single polymer composites by partially melting recycled polyamide 6 fibers: preparation and characterization," J. Appl. Polym. Sci., 2010. 118(6): p. 3357-3363 (7 pages).
Goyal, R. K. et al., "High performance polymer composites on PEEK reinforced with aluminum oxide," J. Appl. Polym. Sci., 2006. 100(6): p. 4623-4631 (9 pages).
Groner, M. D. et al., "Gas Diffusion Barriers on Polymers Using Al2O3 Atomic Layer Deposition," Applied Physics Letters 88, 051907, 2006 (3 pages).
Han, Dong K. et al., "In vivo biostability and calcification-resistance of surface-modified PU-PEO-SO3," Journal of Biomedical Materials Research, vol. 27, 1063-1073, 1993 (11 pages).
Hass, D. D. et al., "Reactive vapor deposition of metal oxide coatings," Surface and Coatings Technology 146-147 (2001) 85-93, 9 pages.
Hine, P.J. et al., "High stiffness and high impact strength polymer composites by hot compaction of oriented fibers and tapes.," in Mechanical Properties of Polymers Based on Nanostructure and Morphology, CRC Press, 2005 (45 pages).
Hine, P.J. et al., "Hot compaction of woven nylon 6,6 multifilaments," J. Appl. Polym. Sci., 2006. 101(2): p. 991-997 (7 pages).
Hine, P.J. et al., "Hot Compaction of Woven Poly(ethylene terephthalate) Multifilaments," J. Appl. Polym. Sci., 2004. 91(4): p. 2223-2233 (11 pages).
Hine, P.J. et al., "Hybrid carbon fibre/nylon 12 single polymer composites," Composites Part A: Applied Science and Manufacturing 65 (2014) (17 pages).
"International Preliminary Report on Patentability," for International Application No. PCT/US2013/048976 dated Jan. 6, 2015 (9 pages).
"International Preliminary Report on Patentability," for PCT Application No. PCT/US2016/024614 dated Oct. 19, 2017 (7 pages).
"International Preliminary Report on Patentability," for PCT Application No. PCT/US2016/024753 dated Oct. 19, 2017 (7 pages).
"International Preliminary Report on Patentability," for PCT Application No. PCT/US2016/039808 dated Jan. 11, 2018 (8 pages).
"International Preliminary Report on Patentability," for PCT Application No. PCT/US2016/041757 dated Jan. 25, 2018 (8 pages).
"International Preliminary Report on Patentability," for PCT Application No. PCT/US2016/050691 dated Mar. 29, 2018 (9 pages).
"International Preliminary Report on Patentability," for PCT Application No. PCT/US2017/032656 dated Nov. 29, 2018 (7 pages).
"International Search Report & Written Opinion," for International Application No. PCT/US2013/048976, dated Nov. 19, 2013 (20 pages).
"International Search Report and Written Opinion," for PCT Application No. PCT/US2016/041757 dated Oct. 12, 2016 (12 pages).
"International Search Report and Written Opinion," for PCT application No. PCT/US2016/050691 dated Dec. 19, 2016 (14 pages).
"International Search Report and Written Opinion," for PCT Application No. PCT/US2017/032656 dated Jul. 21, 2017 (16 pages).
"International Search Report and Written Opinion," for PCT Application No. PCT/US2018/028864 dated Jul. 30, 2018 (10 pages).
"International Search Report and Written Opinion," for PCT/US2016/024614 dated Jul. 12, 2016 (13 pages).
"International Search Report and Written Opinion," for PCT/US2016/024753 dated Jul. 22, 2016 (11 pages).

(56) References Cited

OTHER PUBLICATIONS

"International Search Report and Written Opinion," for PCT/US2016/039808 dated Sep. 26, 2016 (11 pages).
Jen, Shih-Hui et al., "Critical tensile and compressive strains for cracking of al2O3 films grown by atomic layer deposition," Journal of Applied Physics 109, 084305 (2011), 11 pages.
Jen, Shih-Hui et al., "Critical tensile strain and water vapor transmission rate for nanolaminate films grown using al2o3 atomic layer deposition and alucone molecular layer deposition," Applied Physics Letters 101, 234103 (2012), 3 pages.
Jiang, Shaoyi et al., "Ultralow-Fouling, Functionalizable, and Hydrolyzable Zwitterionic Materials and Their Derivatives for Biological Applications," Adv Mater. Mar. 5, 2010;22(9):920-32 (13 pages).
Kalejs, et al., "St. Jude Epic Heart Valve Bioprostheses Versus Native Human and Porcine Aortic Valves—Comparison of Mechanical Properties," Interactive Cardiovascular and Thoracic Surgery 8 (2009) 553-557.
Kalfon-Cohen, Estelle et al., "Microstructure and nematic transition in thermotropic liquid crystalline fibers and their single polymer composites," Polym. Adv. Technol., 2007. 18(9): p. 771-779 (9 pages).
Kang, Jungmee et al., "Polyisobutylene-Based Polyurethanes with Unprecedented Properties and How They Came About," Journal of Polymer Science Part A: Polymer Chemistry, 2011. 49(18): p. 3891-3904 (14 pages).
Khondker, O.A. et al., "Fabrication and mechanical properties of aramid/nylon plain knitted composites," Composites Part A: Applied Science and Manufacturing, 2004. 35(10): p. 1195-1205 (11 pages).
Kim, Nam K. et al., "Nanofibrillar Poly(vinylidene fluoride): Preparation and Functional Properties," Int. J. Polym. Mater. Polym. Biomater., 2014. 63(1): p. 23-32 (10 pages).
Kim, Nam K. et al., "Polymer-Polymer and Single Polymer Composites Involving Nanofibrillar Poly(vinylidene Fluoride): Manufacturing and Mechanical Properties," J. Macromol. Sci., Part B: Phys., 2014. 53(7): p. 1168-1181 (14 pages).
Kuang, Jinghao et al., "Universal Surface-initiated Polymerization of Antifouling Zwitterionic Brushes Using a Mussel Mimetic Peptide Initiator," Langmuir. May 8, 2012; 28(18): 7258-7266 (20 pages).
Lane, Bobby "What Line Should I Use?," Bassmaster.com (www.bassmaster.com/tips/ask-experts-what-line-should-i-use) Apr. 2013, 1-7.
"Liquid-Crystal Polymer," Wikipedia, the Free Encyclopedia <http://en/wikipedia.org/wiki/Liquid-crystal_polymer>, retrieved Jun. 2, 2016 (3 pages).
Liu, et al., "Effect of fiber orientation on the stress distribution within a leaflet of a polymer composite heart valve in the closed position," J of Biomedichanics, 2007, 40:1099-1106 (8 pages).
Mach, H. et al., "Highly Reactive Polyisobutene as a Component of a New Generation of Lubricant and Fuel Additives," Lubrication Science 1999, 11 (2), 175-185 (11 pages).
Madhusha, "Difference between Fluorine and Fluoride," Aug. 9, 2017, PEDIAA.com, pp. 1-8. URL <http://pediaa.com/difference-between-fluorine-and-fluoride/> (8 pages).
Maity, J. et al., "Homocomposites of chopped fluorinated polyethylene fiber with low-density polyethylene matrix," Mater. Sci. Eng., A, 2008. A479(1-2): p. 125-135 (11 pages).
Masoumi, et al., "Trilayered Elastomeric Scaffolds for Engineering Heart Valve Leaflets," Biomaterials. Sep. 2014; 35(27):7774-7785.
Matabola, K. P. et al., "Single polymer composites: a review," Journal of Materials Science, 2009. 44(23): p. 6213-6222 (10 pages).
Mckenna, H. A. et al., "Handbook of Fibre Rope Technology," The Textile Institute, Woodhead Publishing Limited, Cambridge England 2004, 1-432.
Medeiros Araujo, Thiago et al., "Liquid crystalline single-polymer short-fibers composites," Composite Interfaces, 2013. 20(4): p. 287-298 (12 pages).
Mitchell, J. "Braided Fishing Lines (Superlines)," Sufix Fishing Lines Product page as it appeared Apr. 5, 2019 (https://sufix.fishing/braided-fishing-lines-superlines), 1-5.

"Notification of Patent Reexamination," for Chinese Patent Application No. 201380044842.0 dated Feb. 7, 2018 (12 pages) with English summary.
Ohri, Rachit et al., "Hyaluronic acid grafting mitigates calcification of glutaraldehyde-fixed bovine pericardium," J Biomed Mater Res 70A: 328-334, 2004 (7 pages).
Raghavan, R. et al., "Nanocrystalline-to-amorphous transition in nanolaminates grown by low temperature atomic layer deposition and related mechanical properties," Applied Physics Letters 100, 191912 (2012), 9 pages.
Rutledge, G.C. et al., "Electrostatic Spinning and Properties of Ultrafine Fibers," National Textile Center Annual Report: Nov. 2001, M01-D22, (10 pages).
Schneider, Tobias et al., "Influence of fiber orientation in electrospun polymer scaffolds on viability, adhesion and differentiation of articular chondrocytes," Clinical Hemorheology and Microcirculation 52 (2012) 325-336 (13 pages).
"Second Office Action," for Chinese Patent Application No. 201380044842.0, dated Aug. 12, 2016 (16 pages) with summary.
"Second Office Action," for Chinese Patent Application No. 201680018700.0 dated Jul. 12, 2019 (8 pages) No English Translation.
"Second Office Action," for Chinese Patent Application No. 201680036250.8 dated Jul. 11, 2019 (4 pages) No English Translation.
Shin, Y. M. et al., "Experimental characterization of electrospinning: the electrically forced jet and instabilities," Polymer 42 (2001) 9955-9967 (13 pages).
Sun, Xiaoli et al., "α and β Interfacial Structures of the iPP/PET Matrix/Fiber Systems," Macromolecules, 2007. 40(23): p. 8244-8249 (6 pages).
Szeghalmi, Adriana et al., "All dielectric hard x-ray mirror by atomic layer deposition," Applied Physics Letters 94, 133111 (2009), 3 pages.
Szilagyi, Imre M. et al., "Review on One-Dimensional Nanostructures Prepared by Electrospinning and Atomic Layer Deposition," INERA Workshop of ISCMP2014, IOP Publishing, Journal of Physics: Conference Series 559, 2014 (13 pages).
"Third Office Action," for Chinese Patent Application No. 201380044842.0 dated Dec. 29, 2018 (12 pages), with English translation.
Tu, Qin et al., "Synthesis of polyethylene glycol- and sulfobetaine-conjugated zwitterionic poly(l-lactide) and assay of its antifouling properties," Colloids and Surfaces B; Biointerfaces 102 (2013) 331-340 (10 pages).
Vesely, et al., "Micromechanics of the Fibrosa and the Ventricularis in Aortic Valve Leaflets," J Biomech. 1992 25(1):101-113.
Vick, Linda W. et al., "Hot compaction and consolidation of polycarbonate powder," Polym. Eng. Sci., 1998. 38(11): p. 1824-1837 (14 pages).
Wang, Qiang et al., "A novel small animal model for biocompatibility assessment of polymeric materials for use in prosthetic heart valves," J Biomed Mater Res 93A: 442-453, 2010 (12 pages).
Wang, Qiang et al., "In-Vivo Assessment of a Novel Polymer (SIBS) Trileaflet Heart Valve," J Heart Valve Dis, Jul. 2010, 19(4):499-505 (7 pages).
Ward, I.M. et al., "Developments in oriented polymers," Plastics, Rubber and Composites, 2004. 33(5): p. 189-194 (6 pages).
Ward, I.M. et al., "Novel composites by hot compaction of fibers," Polym. Eng. Sci., 1997. 37(11): p. 1809-1814 (6 pages).
Wheatley, et al., "Polyurethane: material for the next generation of heart valve prostheses?," Eur J Cardio-Thoracic Surg, 2000, 17:440-448 (11 pages).
"Why Use Superlines?," Berkley-Fishing.com (www.berkley-fishing.com/Berkley-ae-why-use-superlines.html), 1-6.
Yang, Mingjing et al., "Assessing the Resistance to Calcification of Polyurethane Membranes Used in the Manufacture of Ventricles for a Totally Implantable Artificial Heart," J Biomed Mater Res (Appl Biomater) 48: 648-659, 1999 (12 pages).
Yao, Jian et al., "High Strength and High Modulus Electrospun Nanofibers," Fibers 2014; 2:158-187 (30 pages).

(56) References Cited

OTHER PUBLICATIONS

Yeh, Shiou-Bang et al., "Modification of Silicone Elastomer with Zwitterionic Silane for Durable Antifouling Properties," Langmuir 2014, 30, 11386-11393 (8 pages).
Zhang, Baoyan et al., "Studies of Novel Segmented Copolyether Polyurethanes," Eur. Polym. J., vol. 34, No. 3-4, pp. 571-575 (1998) (5 pages).
Zhang, Zhiping et al., "Effect of Crosslinking and Grafting by 60Co-γ-ray Irradiation on Carbon Black/Polyethylene Switching Materials and Fluoride Resin System in self-regulating Heating Cables," JAERI-Conf, 2000. 2000-001 (JCBSRC '99, the 8th Japan-China Bilateral Symposium on Radiation Chemistry, 1999): p. 202-210 (9 pages).
Zhao, Zeng Hua et al., "Research development of single polymer composite preparation," Gongcheng Suliao Yingyong, 2010. 38(2): p. 81-84, with machine translation (11 pages).
Notice of Allowance for U.S. Appl. No. 15/959,894 dated Oct. 21, 2020 (9 pages).
Office Action for Japanese Patent Application No. 2018-501287 dated Dec. 1, 2020 (9 pages) with English Translation.
First Office Action for Chinese Patent Application No. 201780042303.1 dated Mar. 26, 2020 (16 pages) with English Summary.
Office Action for Japanese Patent Application No. 2017-549776 dated Jun. 2, 2020 (2 pages) no English Translation.
Office Action for JP Patent Application No. 2018-501287 dated Jun. 2, 2020 (4 pages) No English Translation.
Response to Communication Pursuant to Rules 161(1) and 162 EPC for European Patent Application No. 18723271.5 filed May 20, 2020 (11 pages).
Response to First Examination Report for Australian Patent Application No. 2016285561 filed May 18, 2020 (11 pages).
"Notification of Reexamination,"for Chinese Patent Application No. 201380044842.0 dated Sep. 26, 2021 (21 pages) with English translation.
"Response to Non-Final Rejection," dated Jul. 20, 2021 for U.S. Appl. No. 16/413,104, submitted via EFS-Web filed Oct. 19, 2021, 12 pages.
"Notice of Allowance," for U.S. Appl. No. 16/413,104 dated Dec. 24, 2021 (14 pages).
"Second Office Action," for Chinese Patent Application No. 201880024683.0 dated Dec. 9, 2021 (9 pages) with English Summary.
Fazal, Adnan et al., "UHMWPE fibre-based composites: Prestress-induced enhancement of impact properties," Composites Part B, 2014, vol. 66, pp. 1-6 (12 pages).
International Search Report and Written Opinion for PCT Application No. PCT/EP2020/083331 dated Feb. 22, 2021 (12 pages).
Office Action for Japanese Patent Application No. 2018-513335 dated Apr. 6, 2021 (4 pages) No English Translation.
Second Office Action for Chinese Patent Application No. 201680018663.3 dated Dec. 16, 2020 (6 pages) with English Summary.
Second Office Action for Japanese Patent Application No. 2019-557835 dated Mar. 9, 2021 (4 pages) with English Translation.
Final Office Action for U.S. Appl. No. 15/959,894 dated Aug. 17, 2020 (13 pages).
Office Action for Japanese Patent Application No. 2017-552443 dated Sep. 15, 2020 (10 pages) with English Translation.
Office Action for Japanese Patent Application No. 2018513335 dated Aug. 4, 2020 (5 pages) with English Translation.
Office Action for Japanese Patent Application No. 2019-557835 dated Sep. 8, 2020 (6 pages) with English Translation.
Response to Communication Pursuant to Article 94(3) EPC for European Patent Application No. 16715218.0 filed Aug. 13, 2020 (15 pages).
Response to Final Rejection dated Aug. 17, 2020 for U.S. Appl. No. 15/959,894, submitted via EFS-Web filed Oct. 9, 2020, 14 pages.
Response to Non-Final Rejection dated May 5, 2020 for U.S. Appl. No. 15/959,894, submitted via EFS-Web filed Aug. 4, 2020, 11 pages.
"Rejection Decision," for Chinese patent application No. 201880024683.0 dated Apr. 15, 2022 (8 pages) with English Summary.
"Communication Pursuant to Article 94(3) EPC," for European Patent Application No. 18723271.5 dated Feb. 16, 2022 (6 pages).

\* cited by examiner

PROSTHETIC VALVES, VALVE LEAFLETS AND RELATED METHODS

This application is a continuation application of U.S. application Ser. No. 15/595,176, filed May 15, 2017, which claims the benefit of U.S. Provisional Application No. 62/338,722, filed May 19, 2016, the contents of all of which are herein incorporated by reference.

FIELD

Aspects herein relate to prosthetic valves, valve leaflets and related methods. More specifically, aspects herein relates to fibrous valve leaflets and valves including the same.

BACKGROUND

Heart function can be significantly impaired when a heart valve is not functioning properly. Potential causes for heart valve malfunction include dilation of an annulus around the valve, ventricular dilation, and a prolapsed or misshapen valve leaflet. When the heart valve is unable to close properly, the blood within a heart chamber can regurgitate, or leak backwards through the valve.

Valve regurgitation may be treated by replacing or repairing a diseased valve, such as an aortic valve. Surgical valve replacement is one method for treating the diseased valve, but other less invasive methods of treatments are also available to many patients. Minimally invasive methods of treatment, such as transcatheter aortic valve replacement (TAVR), generally involve the use of delivery catheters that are delivered through arterial passageways or other anatomical routes into the heart to replace the diseased valve with an implantable prosthetic heart valve. Leaflets of such valves have been formed from various materials including synthetic materials and animal tissues.

SUMMARY

Aspects herein include prosthetic valves, valve leaflets and related methods. In an example, a prosthetic valve is included. The prosthetic valve can include a plurality of leaflets. The leaflets can each have a root portion and an edge portion substantially opposite the root portion and movable relative to the root portion to coapt with a respective edge portion of at least one of the other leaflets of the plurality of leaflets. The leaflets can include a fibrous matrix, the fibrous matrix including polymeric fibers having an average diameter of about 10 nanometers to about 10 micrometers. A coating can surround the polymeric fibers within the fibrous matrix. The coating can have a thickness of about 3 to about 30 nanometers. The coating can be formed of a material selected from the group consisting of a metal oxide, a nitride, a carbide, a sulfide, or fluoride.

In some examples, the leaflets each have a thickness between an upstream side and a downstream side of about 0.003" (0.0762 mm) to about 0.015" (0.381 mm).

The polymeric fibers can include a polymer selected from the group consisting of poly(ethylene oxide), polyethylene, polyisobutylene polyurethane (PIBU), poly(styrene-block-isobutylene-block-styrene (SIBS), polypropylene, polystyrene, polyvinylchloride, polyisobutylene (PIB), poly(styrene) polyurethanes, polyvinylidene difluoride, poly(methyl methacrylate), polyethylene glycol, polyanilines, polypyrroles, polythiophenes, polyphenols, polyacetylenes, polyphenylenes, polyacrylonitriles, polylactic acids, polycaprolactone, polyglycolides, polyvinyl acetates, cellulose acetate, chitosan, proteins, carbohydrates and copolymers including one or more of these. In some examples, the valve can include a synthetic polymer.

The coating material can include a metal oxide selected from the group consisting of aluminum oxide, titanium dioxide, silicon dioxide, ruthenium oxide, rhodium oxide, palladium oxide, silver oxide, osmium oxide, iridium oxide, platinum oxide and gold oxide. In some examples, the metal oxide comprising aluminum oxide ($Al_2O_3$). In addition, in some examples the coating surrounding the polymeric fibers prevents the penetration of water there through. In addition or alternatively, the coating surrounding the polymeric fibers can include a polymeric layer. In addition or alternatively, the coating surrounding the polymeric fibers can be a multilaminate layer including metal oxide and polymeric sublayers.

In various examples, the strength of the polymeric fibers in the fibrous matrix after implantation and exposure to the in vivo environment is greater than an otherwise identical fibrous matrix lacking the metal oxide coating. In various examples, the fibrous matrix can include a void volume of between 1 and 75%. In various examples, the density of the fibrous matrix is substantially uniform across the thickness of the leaflet. In addition or alternatively, the density of the fibrous matrix can be asymmetric across the thickness of the leaflet. In addition or alternatively, the density of the fibrous matrix is greater on the upstream side of the valve leaflet than on the downstream side of the valve leaflet. In addition or alternatively, the density of the fibrous matrix varies across the width of the leaflet.

In various examples, the valve can include a frame, wherein the leaflets are attached to the frame. In addition or alternatively, the leaflets can be sewn to the frame. In addition or alternatively, the leaflets can be integral with the frame. In addition, or alternatively, the frame can be expandable. In addition, or alternatively, the valve can be a TAVI valve. In addition, or alternatively, the leaflets can assume an open position to allow the flow of blood through the valve and a closed position to block the flow of blood through the valve. In addition, or alternatively, the flexural stiffness of the leaflet is less than 8 g/cm.

In an example, a method of making a valve is included. The method can include depositing polymeric fibers in a layer to form a fibrous matrix, cutting the fibrous matrix into the shape of a valve leaflet and applying a layer of a metal oxide onto the polymeric fibers using a gas phase deposition technique. In various aspects, the method can further include attaching the valve leaflet onto a frame. In various examples, the gas phase deposition technique comprising atomic layer deposition (ALD). In addition or alternatively, depositing the polymeric fibers includes electrospinning. In addition or alternatively, depositing the polymeric fibers includes weaving.

In various examples, the average diameter of the polymeric fibers is about 10 nanometers to about 10 micrometers. In addition or alternatively, the average thickness of the metal oxide layer is about 3 to about 30 nanometers.

In an example, a method of making a valve is included having the steps of depositing polymeric fibers into a mold in a layer to form a fibrous matrix, removing the fibrous matrix from the mold and applying a layer of a metal oxide onto the polymeric fibers using a gas phase deposition technique.

In an example, a method of making a valve is included having the steps of depositing polymeric fibers onto a frame to form a valve leaflet and applying a layer of a metal oxide onto the polymeric fibers using a gas phase deposition technique.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While examples are susceptible to various modifications and alternative forms, specifics thereof have been shown by way of example and drawings, and will be described in detail. It should be understood, however, that the scope herein is not limited to the particular examples described. On the contrary, the intention is to cover modifications, equivalents, and alternatives falling within the spirit and scope herein.

DETAILED DESCRIPTION

The examples described herein are not intended to be exhaustive or to limit the scope to the precise forms disclosed in the following detailed description. Rather, the examples are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Leaflets of such prosthetic valves can be formed from various materials including synthetic materials and animal tissues. Synthetic leaflets should be designed to withstand repetitive stresses over a substantial length of time.

Electrospun and/or woven fibers can be formed into a layer and can successfully withstand such repetitive stresses. However, partly due to their small diameter which effectively increases the surface area to mass ratio, some fibers can degrade over time in the in vivo environment.

Examples herein include valve leaflets formed with small diameter fibers, such as electrospun fibers and/or woven fibers, that are coated with a layer (such as a metal oxide layer) that prevents degradation of the fibers in vivo.

Figure 1:
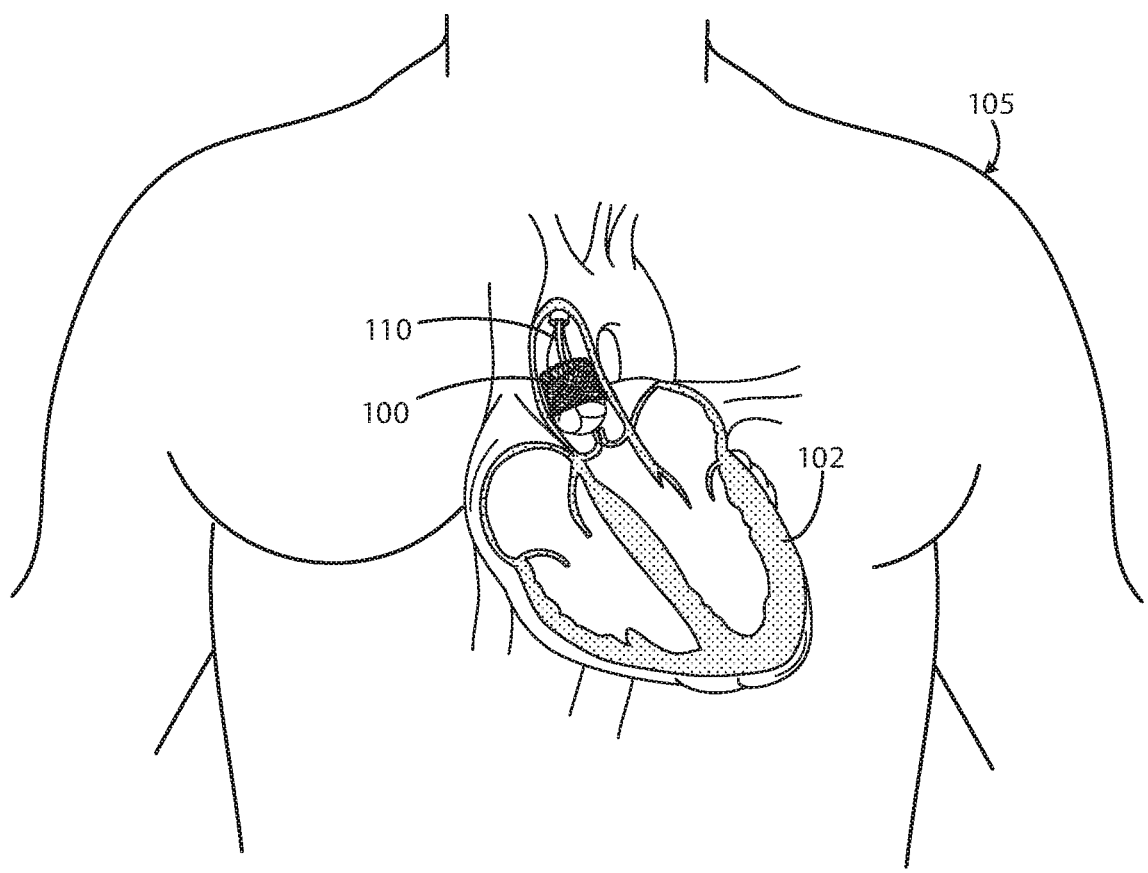
FIG. 1 is a schematic view a prosthetic heart valve within a human body.

FIG. 1 is an illustration of a prosthetic heart valve 100 provided herein within a heart 102 of a human body 105. The heart has four heart valves: a pulmonary valve, a tricuspid valve, an aortic valve and a mitral valve. The heart valves allow blood to pass through the heart and into major blood vessels connected to the heart, for example, the aorta and pulmonary artery. Prosthetic heart valve 100 of FIG. 1 is an aortic prosthetic heart valve that can be surgically implanted or delivered through blood vessels using a delivery device or catheter 110. The delivery catheter 110 can be inserted into a femoral, subclavian, or an aortic incision during a transcatheter aortic valve replacement (TAVR) procedure. Once inserted, the delivery catheter 110 can deliver the prosthetic heart valve 100 to the desired location within the anatomy and release the heart valve 100 at a desired implantation site. Although FIG. 1 shows prosthetic heart valve 100 replacing an aortic valve, in some cases, prosthetic heart valve 100 can be a replacement for another type of heart valve (e.g., a mitral valve or a tricuspid valve). In some examples the heart valve is specifically a TAVI (transcatheter aortic valve implantation) valve.

Figure 2:
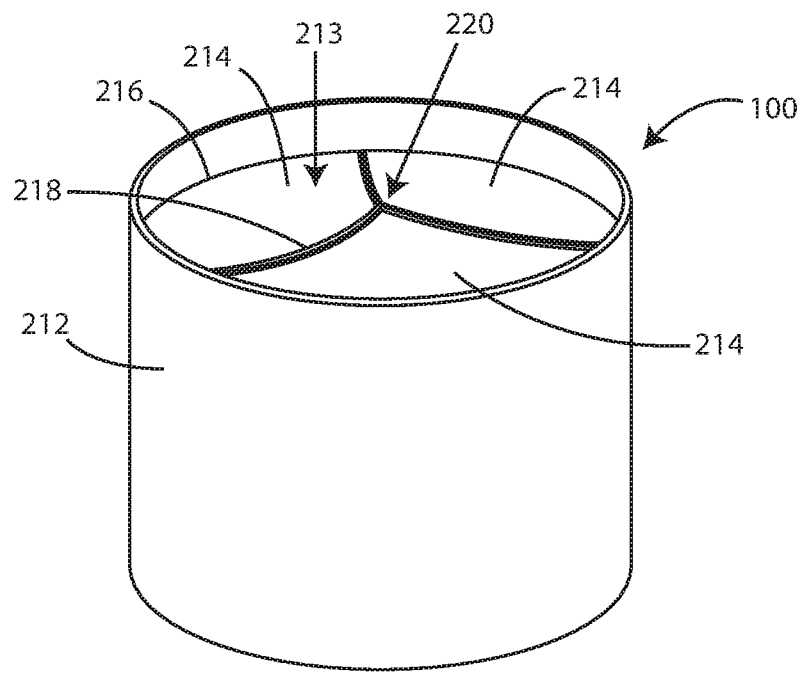
FIG. 2 is a schematic perspective view of a prosthetic heart valve in accordance with various examples herein.

Referring to FIG. 2 the prosthetic heart valve 100 includes a base 212 defining a substantially cylindrical passage 213 and a plurality of polymeric leaflets 214 disposed along the substantially cylindrical passage 213. Each polymeric leaflet 214 includes a respective root portion 216 coupled to the base 212 and a respective edge portion 218 movable relative to the root portion 216 to coapt with the edge portions of the other polymeric leaflets along the coaptation region 220. It should be appreciated that the prosthetic heart valve 100 can be any type of heart valve (e.g., a mitral valve or an aortic valve).

Figure 3:
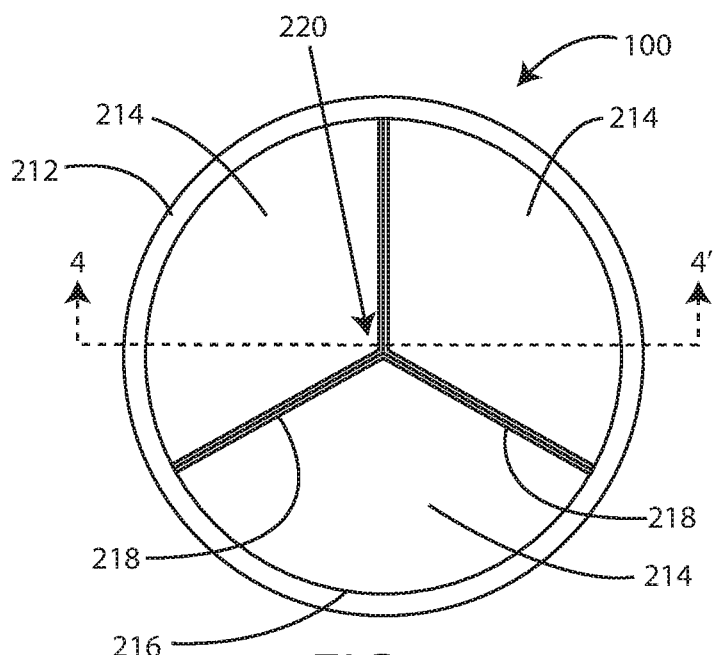
FIG. 3 is a schematic top view of a prosthetic heart valve.

In use, the prosthetic heart valve 100 is implanted (e.g., surgically or through transcatheter delivery) in a mammalian heart. The edge portions 218 of the leaflets 214a move into coaptation with one another in a closed position to substantially restrict fluid from flowing past the prosthetic heart valve 100 in a closed position. The edge portions 218 of the leaflets 214 move away from one another to an open position permitting fluid to flow past the prosthetic heart valve 100. Movement of the leaflets 214 between the closed and open positions substantially approximates the hemodynamic performance of a healthy natural valve. FIG. 3 shows a top view of the prosthetic heart valve 100.

Figure 4:
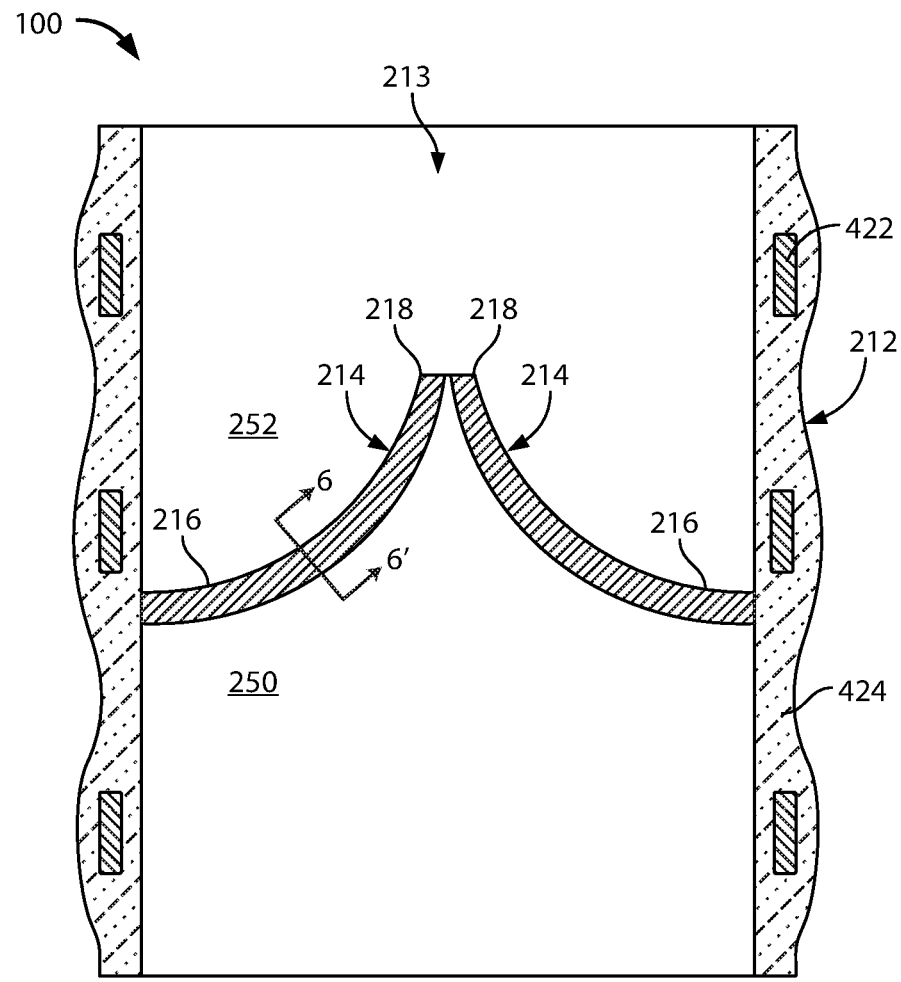
FIG. 4 is a schematic cross-sectional view of an artificial heart valve as taken along line 4-4' of FIG. 3.

Referring now to FIG. 4, a cross-sectional view of elements of a prosthetic heart valve are shown as taken along line 4-4' of FIG. 3. The base 212 includes a frame 422 disposed in a polymer layer 424. However, in other examples, the frame 422 may not be disposed in a polymer layer. In some examples, the respective root portions 216 of the leaflets 214 can be attached to the base 212 using a mechanical mechanism, a fastener, sutures or can otherwise be sewn on. Additionally or alternatively, the polymer layer 424 can be disposed between each of the leaflets 214 and the frame 422 such that the polymer layer 424 protects the leaflets 214 from inadvertent contact with the frame 422

(e.g., as can occur through eccentric deformation of the prosthetic heart valve 100 on a calcium deposit present at the implantation site).

The frame 422 is substantially cylindrical such that the outer surface of the base 212 is substantially cylindrical and the polymer layer 424 disposed on the frame 422 forms the substantially cylindrical passage 213. The frame 422 can provide a radial force sufficient to at least partially secure the valve 100 in place at the implantation site. In some implementations, the frame 422 is radially expandable from a collapsed position (e.g., for transcatheter delivery) to an expanded position (e.g., for positioning at the implantation site). For example, the frame 422 can be a self-expandable stent or a balloon-expandable stent.

The frame can be formed of various materials. By way of example, the frame can be formed of a metal, a polymer, a ceramic, a composite, or the like. In some examples, the frame can be formed of a polymer and a metal oxide layer can be disposed over the polymeric frame. The metal oxide layer can be applied in various ways, including ALD techniques described herein.

The frame 422 is completely disposed in the polymer layer 424, with the polymer layer 424 forming a contoured outer surface of the valve 10. However, in some implementations, the frame 422 is partially disposed in the polymer layer 424. In certain implementations, the polymer layer 424 is applied to the frame 422 to form a substantially smooth inner and/or outer surface of the valve 100. The valve 100 and the leaflets 214 have an upstream side 250 and a downstream side 252.

Figure 5:
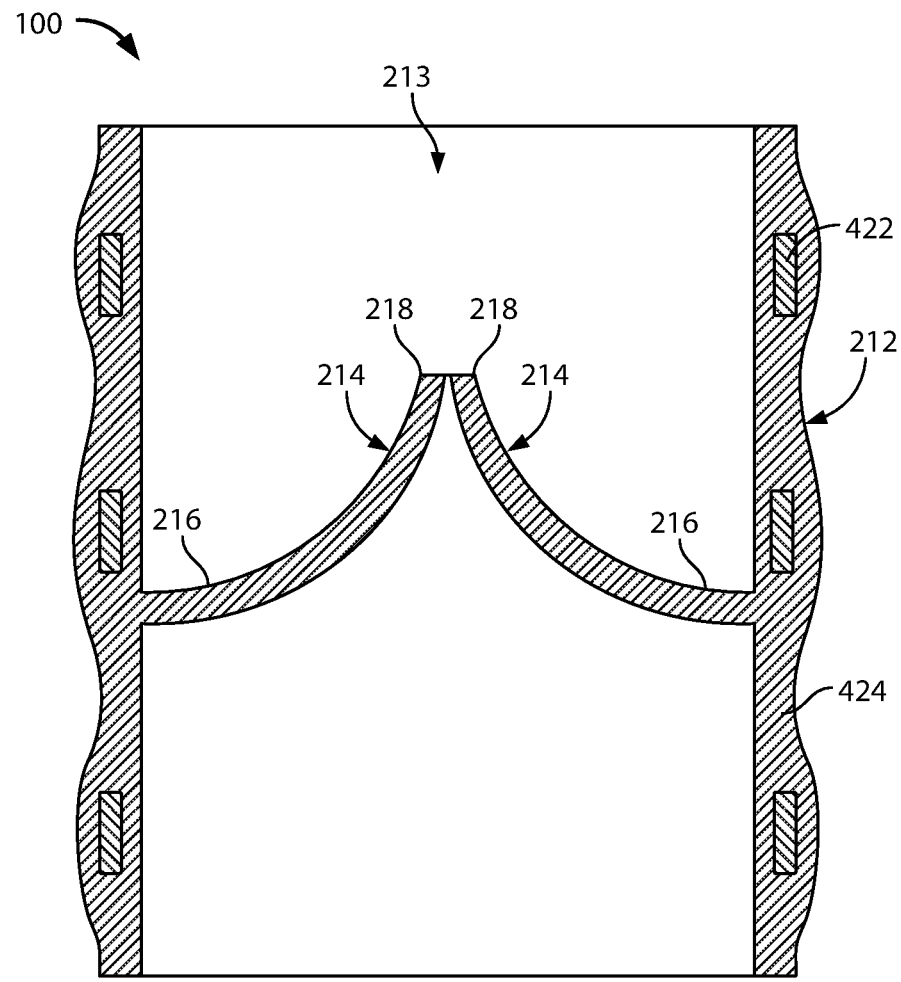
FIG. 5 is a schematic cross-sectional view of an artificial heart valve in accordance with various examples.

In some examples the valve leaflets can be integral with the frame and/or a polymer layer disposed over the frame. Referring now to FIG. 5, a schematic cross-sectional view is shown of an artificial heart valve in accordance with various examples. In this view, the valve leaflets 214 are integral with the polymer layer 424. The polymer layer 424 can form a substantially continuous surface with the respective root portions 416 of the leaflets 214. This can reduce the likelihood of stress concentrations at the junction of the respective root portions 216 and the base 212.

In this particular embodiment, the root portions 216 are secured to the polymer layer 224 and, thus, the base 212 without the use of sutures, the base 212 can be formed without support portions typically required on sutured valves. This can facilitate formation of the prosthetic heart valve 100 with a lower overall height as compared to sutured valves. Such lower overall height can improve the hemodynamic performance of the prosthetic heart valve as compared to valves having larger overall heights.

Additionally or alternatively, the lower overall height facilitated by the formation of the prosthetic heart valve 100 without sutures can improve the physiological performance of the prosthetic heart valve 100 as compared to valves having larger overall heights. For example, the base 212 can define an overall height of the prosthetic heart valve 100 and the height of the base 212 can be sized such that the coronary ostium is not covered by the prosthetic heart valve 100 at the implantation site. This can, for example, reduce the likelihood of disrupting normal electrical signaling in the heart. In some implementations, the base 212 has an overall height of about 5 mm to about 20 mm, depending on the diameter of the cylindrical valve body.

In some examples the polymeric leaflets 214 each have a substantially uniform thickness along a length of the leaflet extending from each respective root portion 216 to the respective edge portion 218. In other examples the polymeric leaflets 214 have a thickness that varies along a length of the leaflet extending from each respective root portion 216 to the respective edge portion 218.

The natural anatomical construction of a heart valve is such that there are anisotropic mechanical properties. The structure of the native leaflet is a trilayer construct. On the side facing the ventricle, there is a layer of collagen and elastin fibers with a radial orientation (aligned from the wall of the supporting structure to the tip of the valve leaflet). In the fibrosa layer (the side facing the aorta) there is collagen but the fibers are oriented more circumferentially, which imparts characteristic flexibility and enables valve sealing. It should be appreciated that various parameters of the materials of the leaflets of the present disclosure such as stiffness, thickness, density, and the like can be varied along the leaflets 214 to substantially match the anisotropic mechanical properties of healthy, native leaflets. In some examples, the flexural stiffness of the leaflet (e.g., leaflet 214) is less than 8 g/cm.

Figure 6:
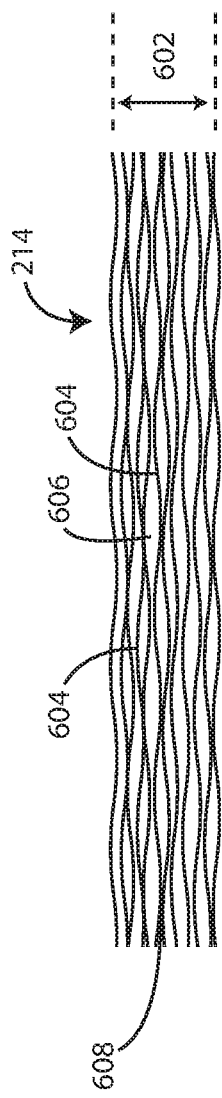
FIG. 6 is a schematic cross-sectional view of a portion of a valve leaflet in accordance with some examples herein.

FIG. 6 is a schematic cross-sectional view of a portion of a valve leaflet in accordance with some examples herein as taken along line 6-6' of FIG. 4. The valve leaflet 214 includes a plurality of fibers 604. This view is provided by way of example and it will be appreciated that the actual orientation of fibers within the layer may be substantially more random than as shown in FIG. 6, depending on the technique used for deposition of the fibers. The fibers 604 form a fibrous matrix or fibrous layer 608. The fibrous layer 608 can include a substantial number of pores 606 or voids. The density of the fibrous matrix is such that the void volume is between 1 and 75 percent of the total volume of the fibrous matrix. In some examples, the density of the fibrous matrix is substantially uniform across the thickness of the leaflet. In some examples, the density of the fibrous matrix is asymmetric across the thickness of the leaflet. In some examples, the density of the fibrous matrix is greater on the upstream side of the valve leaflet than on the downstream side of the valve leaflet. In some examples the density of the fibrous matrix varies across the width of the leaflet.

The thickness of the fibrous layer 608 can vary. In some examples the fibrous layer 608 can be from about 0.002" (0.0508 mm) to about 0.02" (0.508 mm) thick. In some examples the fibrous layer 608 can be from about 0.003" (0.0762 mm) to about 0.015" (0.381 mm) thick.

Figure 7:
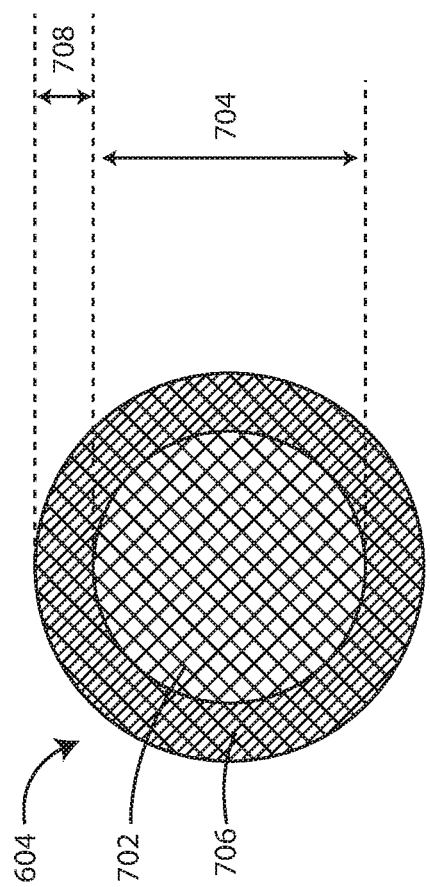
FIG. 7 is a schematic cross-sectional view of a fiber in accordance with various examples herein.

FIG. 7 is a schematic cross-sectional view of a fiber 604 in accordance with various examples herein. The fiber 604 can include a polymeric core 702 and a shell or coating 706. The polymeric core 702 can have a thickness or diameter 704 in the ranges described below. However, in some examples, the diameter 704 is from about 10 nanometers to about 10 micrometers. Exemplary materials for the polymeric core 702 of fibers are described in greater detail below.

If the coating layer(s) on the polymeric fiber are too thick, the flexibility of the fiber can be adversely impacted. If the coating layer(s) are too thin, it will be ineffective to prevent migration of water and other components and therefore ineffective to prevent the degradation of the fibers. The coating (or shell) 706 can have a thickness 708 of about 3 to about 30 nanometers. In some examples, the coating 706 is greater than or equal to about 2, 3, 4, 5, 6, 8, 10, 12, 14, 16, 18, 20, 22, 24, 26 or 28 nanometers. In some examples, the coating 706 is less than or equal to about 30, 28, 26, 24, 22, 20, 18, 16, 14, 12, 10, 8 or 6 nanometers. In some examples these thicknesses can apply to the sum of all coatings applied to the polymeric core. In some examples these thickness can apply to individual layers making up the entire coating on the polymer core. Exemplary materials for the coating 706 are described in greater detail below.

Figure 8:
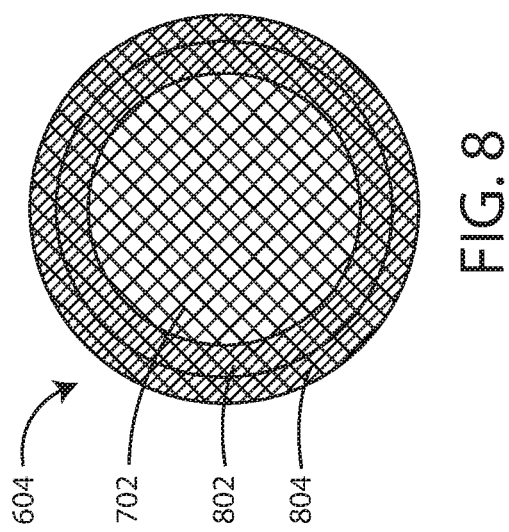
FIG. 8 is a schematic cross-sectional view of a fiber in accordance with various examples herein.

In some examples, the fiber can include more than one layer (or coating layer) disposed over the polymer core. Referring now to FIG. 8, a schematic cross-sectional view of a fiber 604 in accordance with various examples is shown. The fiber 604 can include a polymeric core 702, and a shell or coating including a first layer 802 disposed over the polymeric core and a second layer 804 disposed over the first layer 802. The first layer 802 and second layer 804 can be formed of different materials. In some examples, at least one of the first and second layers can be formed of a metal oxide and at least one of the first and second layers can be formed of a polymer.

Figure 9:
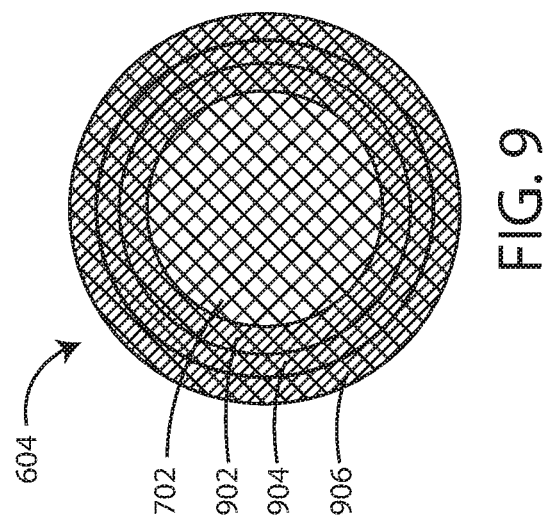
FIG. 9 is a schematic cross-sectional view of a fiber in accordance with various examples herein.

Referring now to FIG. 9, a schematic cross-sectional view of a fiber 604 in accordance with various examples is shown. The fiber 604 can include a polymeric core 702, a first layer 902 disposed over the polymeric core, a second layer 904 disposed over the first layer 902, and a third layer disposed over the second layer 904. The first layer 902, second layer 904 and third layer 906 can be formed of different materials. In some examples, one or more of the layers that are not contacting each other can be formed of the same materials. While FIG. 9 illustrates three coating layers, it will be appreciated that in various examples herein even more than three coating layers can be used. In some examples, there are from 1 to 9 coating layers. In some examples, there are from 2 to 5 coating layers.

Figure 10:
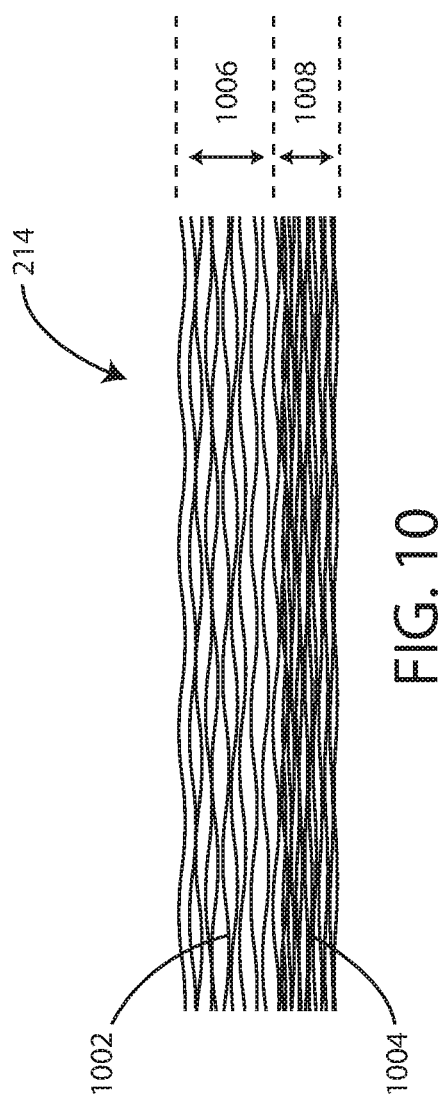
FIG. 10 is a schematic cross-sectional view of a portion of a valve leaflet in accordance with various examples herein.
Figure 11:
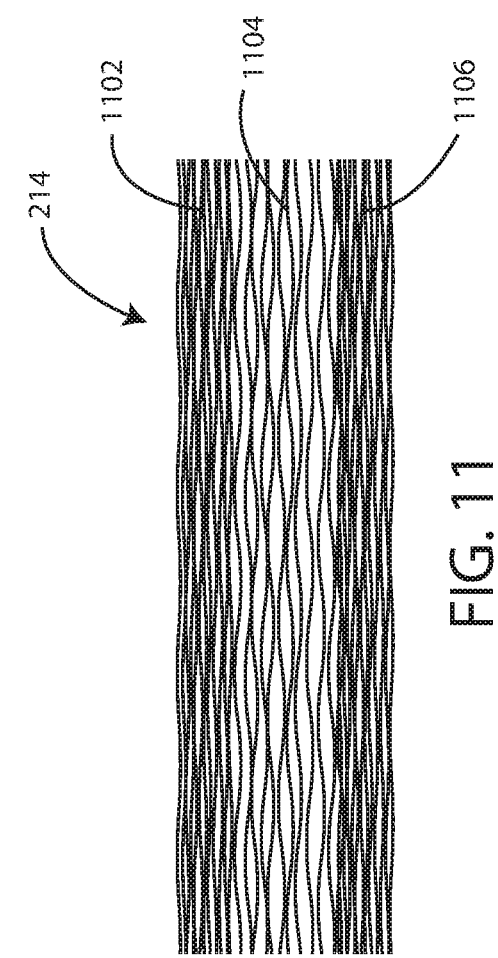
FIG. 11 is a schematic cross-sectional view of a portion of a valve leaflet in accordance with various examples herein.

In some examples different zones or portions of fibers can have different properties. By way of example, different zones or layers of fibers can have different densities of fibers (for example, as measured by void space). In some examples, different zones can be formed of polymeric fibers with different properties, such as different polymer compositions, different diameters, etc. FIG. 10 is a schematic cross-sectional view of a portion of a valve leaflet 214 in accordance with various examples herein. The valve leaflet 214 can include a first zone or portion 1004 and a second zone or portion 1002. The first zone or portion 1004 can have a first thickness 1008 and the second zone or portion 1002 can have a second thickness 1006. The first thickness 1008 and the second thickness 1006 can either be the same or different. FIG. 11 is a schematic cross-sectional view of a portion of a valve leaflet 214 in accordance with various examples herein. The valve leaflet 214 can include a first zone or portion 1106, a second zone or portion 1104 and a third zone or portion 1102. In some examples, the first zone or portion can be the same as the third zone or portion, while the second zone or portion can be different. In some examples, all of the first zone, second zone, and third zone can be different from one another.

Polymeric Fibers

Fibers herein can be formed of various materials including, specifically, polymers. The fibers can include a polymeric material such as a polymer, or a blend of polymers. A "polymer" is any macromolecule composed of two or more monomers, and includes dimers, trimers, tetramers, etc. A "monomer" is a polymerizable molecule. Typically, the polymeric materials comprise polymer molecules having a median number of monomers that numbers in the tens (10 to 99), in the hundreds (100 to 999), in the thousands (1,000 to 9,999), or in the tens of thousands (10,000 to 99,999) as well as a mixture of polymers having different median numbers of monomers. The polymeric materials can comprise polymer molecules having a median number of monomers that is 100,000 or more.

Polymers herein can be crosslinked or uncrosslinked, linear or branched, natural or synthetic, thermoplastic or thermosetting, and may be biostable, biodegradable, bioabsorbable, biodisintegrable, or dissolvable.

Exemplary polymers can include those that are capable of being electrospun. Exemplary polymers can include, but are not limited to, poly(ethylene oxide), polyethylene, polyisobutylene polyurethane (PIBU), poly(styrene-block-isobutylene-block-styrene (SIBS), polypropylene, polystyrene, polyvinylchloride, polyisobutylene (PIB), poly (styrene) polyurethanes, polyvinylidene difluoride, poly (methyl methacrylate), polyethylene glycol, polyanilines, polypyrroles, polythiophenes, polyphenols, polyacetylenes, polyphenylenes, polyacrylonitriles, polylactic acids, polycaprolactone, polyglycolides, polyvinyl acetates, cellulose acetate and copolymers including one or more of these. Polymers can also include biological polymers such as chitosan, proteins, carbohydrates, and the like.

The fibers can be formed in various ways. In some examples, the fibers can be formed through an electrospinning (or electrostatic fiber formation or electrospraying) process. Electrospinning is a fiber production method which uses electric force to draw charged threads of polymer solutions or polymer melts. When a sufficiently high voltage is applied to a liquid droplet, the body of the liquid becomes charged, and electrostatic repulsion counteracts the surface tension and the droplet is stretched. At a critical point a stream of liquid erupts from the surface. This point of eruption is known as the Taylor cone. If the molecular cohesion of the liquid is sufficiently high, stream breakup does not occur and a charged liquid jet is formed. As the jet dries in flight, the mode of current flow changes from ohmic to convective as the charge migrates to the surface of the fiber. The jet is then elongated by a whipping process caused by electrostatic repulsion initiated at small bends in the fiber, until it is finally deposited on the grounded collector. The elongation and thinning of the fiber resulting from this bending instability leads to the formation of substantially uniform fibers with nanometer-scale diameters.

The two principal parameters that control behavior of the Taylor cone are the viscosity and voltage at the nozzle. Exemplary methods of creating ultra-thin fibers for use in creating a fiber meshwork involve electro-spinning. Electrospinning methods are described in Shin, Hohman, Brenner, and Rutledge, "Experimental Characterization of electrospinning: the electrically forced jet and instabilities", Polymer 42, 9955-9967, (2001), incorporated herein by reference in its entirety. Fibers that are micrometers in diameter can be created by melt spinning or gel spinning, i.e., they are formed out of a gel or a molten melt.

A particularly exemplary method of depositing the fiber meshwork, is to use a process referred to as flow-limited field-injection electrostatic spraying (FFESS). FFESS is a form of electrospraying which offers a very high degree of control over shape and flow regimes, and which allows spinning a fiber-meshwork on top of a medical device, such as an endoprosthesis, with a glass spray nozzle. The nozzle generates a charge at the liquid meniscus that enables successful electrospray. The two principal differences between conventional electro-spraying (CES) and FFESS are first that FFESS sprays a polymer/solvent solution from a smooth glass capillary whereas CES uses a metal hypodermic needle, and second that FFESS uses a sharpened tungsten needle inside capillary, whereas CES has no analogous structure. The overall effect of the FFESS apparatus is to improve jet stability and uniformity of the polymer sprayed by FFESS relative to that from CES.

Using the FFESS method for electro-spinning creates a fiber meshwork in which the one or more fibers have a highly controlled fiber diameter. In particular, as would be understood by one of ordinary skill in the art, by controlling the voltage, flow-rate, concentration of polymer in the spray fluid, the viscosity of the spray fluid, and the distance of the nozzle from the surface of the underlying structure (e.g., a mold or a valve frame, or a pocket within a valve frame), the diameter of the fibers formed during the spinning process can be controlled. For exemplary descriptions of the various factors, see, e.g., "Electrostatic Spinning and Properties of Ultrafine Fibers", Rutledge, et al., National Textile Center Annual Report, M01-D22, (November 2001), incorporated herein by reference. See also further description on the internet at www.che.vt.edu/Wilkes/electrospinning/electr-spinning.html. It is also consistent with the fiber meshwork that the diameter of the fibers can be changed during deposition.

A further advantage of FFESS is thus that, because of the high degree of control of the fiber diameter, if the weight of the fiber meshwork as well as the density of the polymer material for a given fiber diameter are known, the total surface area of the meshwork can be precisely calculated. Thus, the surface area of a fiber of diameter d, and of length l, assuming a uniform perfectly cylindrical constant cross-section along its length, is $\pi dl$, ignoring contributions from the ends of the fibers. FFESS is further described in "Controlling surface nano-structure using flow-limited field-injection electrostatic spraying (FFESS) of poly(d,l-lactide-co-glycolide)", Berkland, Pack, and Kim, Biomaterials, 25: 5649-5658, (2004) and U.S. Patent Application Publication No. 2004/0022939, both of which are incorporated herein by reference in their entirety.

Solvents used during the electrospinning process can affect various aspects such as fiber morphology. Solvents used can include, but are not limited to, dichloromethane, chloroform, methanol, tetrahydrofuran, ethyl acetate, ethanol, methyl ethyl ketone, dichloroethane, water, dimethylformamide, and combinations including one or more of these. In some examples, the solution conductivity can be manipulated in order to impact fiber diameter and morphology. By way of example, various salts (including but not limited to sodium chloride and phosphate salts) can be added with the solvent in order to change the solution conductivity.

Beyond electrospinning, it will be appreciated that fibers can be formed, deposited and/or formed into components of a valve in other ways. For example, in some examples, fibers can be woven. In some examples fibers can be woven to form a fibrous matrix forming at least part of a valve leaflet. Many different weaving techniques are contemplated herein.

Other techniques of forming fibers herein can include, but are not limited to, spinning, centrifugal spinning (force spinning), drawing, template synthesis, phase separation, melt-blowing, self-assembly and the like.

Diameters of the polymeric core of fibers used herein can be greater than about 5, 10, 20, 30, 50, 100, 150, 200, 250, 500, 750, or 1000 nanometers. In some examples the diameter of the polymeric core of fibers herein can be greater than about 1, 2, 3, 4, 5, 6, 7, or 8 micrometers. Diameters of the polymeric core of fibers used herein can be less than about 20, 18, 16, 14, 12, 10, 8, 6, 4, 2 or 1 micrometer. In some examples, diameters of the polymeric core of fibers used herein can be less than about 1000, 900, 800, 700, 600, 500, 400, 200, 100, or 50 nanometers. Diameters of the polymeric core of fibers used herein can be within a range wherein any of the foregoing numbers can serve as the lower or upper bound of the range, provided that the lower bound is less than the upper bound. In some examples, the average diameter of the polymeric core can be from about 10 nanometers to about 10 micrometers.

Coating Layers and Deposition

Examples herein can include fibers wherein a coating or layer of material is disposed on a polymeric fiber. In various examples, the coating or layer can completely encapsulate the fiber in that it can surround the fiber on all sides. In various examples, the thickness of the coating or layer can be approximately equal on all sides.

The coating or layer can include various materials. Exemplary materials can include, but are not limited to, metal oxides, nitrides, carbides, sulfides, and fluorides.

Materials can be deposited in various ways. In various examples, a thin film deposition technique is used. Exemplary techniques can include vapor deposition techniques such as physical vapor deposition (PVD), electron beam physical vapor deposition (EB-PVD), hot-filament chemical vapor deposition (HFCVD), hot-filament metal oxide deposition (HFMOD), plasma-assisted chemical vapor deposition, aerosol-chemical vapor deposition (ACVD).

In some examples the materials can be deposited using a technique known as atomic layer deposition (ALD). Atomic layer deposition is a thin film deposition method in which a film is grown on a substrate by exposing its surface to alternate gaseous species (typically referred to as precursors). In contrast to chemical vapor deposition, the precursors are not present simultaneously in the reactor, but they are inserted as a series of sequential, non-overlapping pulses. In each of these pulses the precursor molecules react with the surface in a self-limiting way, so that the reaction terminates once all the reactive sites on the surface are consumed. Consequently, the maximum amount of material deposited on the surface after a single exposure to all of the precursors (a so-called ALD cycle) is determined by the nature of the precursor-surface interaction. By varying the number of cycles it is possible to grow materials uniformly and with high precision on arbitrarily complex and large substrates.

Deposited metal oxides can include, but are not limited to, aluminum oxide ($Al_2O_3$), titanium dioxide ($TiO_2$), silicon dioxide ($SiO_2$) and the like. In some examples, the metal oxide can be a noble metal oxide such as ruthenium oxide, rhodium oxide, palladium oxide, silver oxide, osmium oxide, iridium oxide, platinum oxide and gold oxide.

In some examples, multiple layers of materials can be deposited and those layers can differ from one another. In some examples, the coating can be a nanolaminate including a plurality of thin individual layers that alternate with each other to form a multilayer stack having a total of at least 4 layers. In some examples, the nanolaminate can have at least 8 or at least 10 layers. The individual layers may be metal or ceramic layers. Examples of suitable metals and ceramics for the individual layers of the nanolaminate include $Al_2O_3$, $SiO_2$, $Si_3N_4$, $TiO_2$, BN, ZnO, W, IrOx, $B_2O_3$, $CO_2O_3$, $Cr_2O_3$, $Fe_2O_3$, $Ga_2O_3$, $HfO_2$, $In_2O_3$, MgO, $Nb_2O_5$, NiO, Pd, Pt, $SnO_2$, $Ta_2O_5$, TaN, TaN, AlN, TiCrO, TiN, $VO_2$, $WO_3$, ZnO, (Ta/Al)N, (Ti/Al)N, (Al/Zn)O, ZnS, ZnSe, ZrO, $Sc_2O_3$, $Y_2O_3$, $Ca_{10}(PO_4)(OH)_2$, rare earth oxides, and combinations thereof. In some examples, one of the layers may be $Al_2O_3$, $TiO_2$, W, or $Ta_2O_5$.

Specific examples of useful nanolaminates include structures in which (a) one layer is $Al_2O_3$ and the other layer is $Ta_2O_5$; (b) one layer is $Al_2O_3$ and the other layer is W; and (c) one layer is $Al_2O_3$ and the other layer is $TiO_2$. The individual layers may be amorphous or crystalline.

The layers of the nanolaminate can be formed by atomic layer deposition. Atomic layer deposition is a self-limiting deposition process in which the growth of the monolayer being deposited stops after a certain point (e.g., because of thermodynamic conditions or the bonding nature of the molecules involved), even though sufficient quantities of deposition materials are still available. Atomic layer deposition creates layers that are smooth and uniform U.S. Publ. Pat. Appl. No. 2011/0022160, entitled "Medical Devices Having an Inorganic Coating Layer Formed by Atomic Layer Deposition," which is assigned to the same assignee as the present application and hereby incorporated by reference, describes materials and conditions for using atomic layer deposition to prepare layers on various medical devices. For example, a $TiO_2$ layer can be formed by atomic layer deposition by reacting titanium tetrachloride ($TiCl_4$) and water ($H_2O$) according to the following two sequential half-reactions:

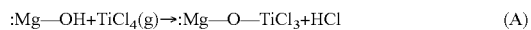  (A)

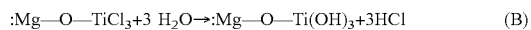  (B)

with :Mg—OH and :Mg—O—$TiCl_3$ being the surface species. These two half-reactions give the overall reaction :Mg—OH+$TiCl_4$+3 $H_2O$→:Mg—O—$Ti(OH)_3$+4 HCl. Titanium tetrachloride and other precursor materials for forming a titanium oxide coating can be obtained from Sigma-Aldrich Corporation of St. Louis, Mo. The choice of deposition temperature is selected based upon the desired crystalline form of the $TiO_2$ layer. The crystalline anatase form of titanium oxide preferentially develops at relatively high deposition temperatures (e.g., greater than 250° C.), whereas the amorphous form of titanium oxide preferentially develops at relatively low deposition temperatures (e.g., less than 150° C.).

Aluminum oxide can be deposited by atomic layer deposition using trimethylaluminum and water as the precursors, and a deposition temperature as low as 50° C. Other examples of suitable reactants and reactant conditions for atomic layer deposition to form layered structures are described, for example, in (a) Fabreguette et al., "X-ray mirrors on flexible polymer substrates fabricated by atomic layer deposition," Thin Solid Films 515:7177-7180 (2007); (b) Szeghalmi et al., "All dielectric hard x-ray mirror by atomic layer deposition," Appl. Phys. Lett. 94:133111 (2009); and (c) Fabreguette et al., "Ultrahigh x-ray reflectivity from W/$Al_2O_3$ multilayers fabricated using atomic layer deposition," Appl. Phys. Lett. 88:013166 (2006).

As noted above, the thickness of the coating or layer can vary. In some examples, the coating is greater than or equal to about 2, 3, 4, 5, 6, 8, 10, 12, 14, 16, 18, 20, 22, 24, 26 or 28 nanometers. In some examples, the coating is less than or equal to about 30, 28, 26, 24, 22, 20, 18, 16, 14, 12, 10, 8 or 6 nanometers. In some examples, the total coating can have a thickness of about 3 to about 30 nanometers. In some examples, individual sublayers can have a thickness of about 1 to about 30 nanometers.

Various methods are included herein. In an example, a method of making a valve is included. The method can specifically include depositing polymeric fibers in a layer to form a fibrous matrix. The method can further include cutting the fibrous matrix into the shape of a valve leaflet. The method can further include applying a layer of a metal oxide onto the polymeric fibers using a gas phase deposition technique. In some examples, the method can further include attaching the valve leaflet onto a frame. The valve leaflet can be attached in various way including through mechanical fixation, adhesives, welding, and the like. In some examples the valve leaflet can be sewn on.

In some examples, a method of making a valve is included. The method can specifically include depositing polymeric fibers into a mold in a layer to form a fibrous matrix. In some examples the method can include removing the fibrous matrix from the mold. In some examples the method can include applying a layer of a metal oxide onto the polymeric fibers using a gas phase deposition technique.

In some examples, a method of making a valve can include depositing polymeric fibers onto a frame to form a valve leaflet and applying a layer of a metal oxide onto the polymeric fibers using a gas phase deposition technique.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this application pertains. All publications and patent applications are herein incorporated by reference to the same extent as if each individual publication or patent application was specifically and individually indicated by reference.

Aspects have been described with reference to various specific and preferred examples and techniques. However, it should be understood that many variations and modifications may be made while remaining within the spirit and scope herein.

The invention claimed is:

1. A prosthetic valve comprising:
   a plurality of leaflets,
   the leaflets each having a root portion and an edge portion substantially opposite the root portion and movable relative to the root portion to coapt with a respective edge portion of at least one of the other leaflets of the plurality of leaflets,
   the leaflets comprising a fibrous matrix, the fibrous matrix comprising polymeric fibers;
   a coating surrounding individual polymeric fibers within the fibrous matrix, the coating comprising a first layer and a second layer,
   wherein one layer of the first layer and the second layer comprises a material selected from the group consisting of a metal oxide, a nitride, a carbide, or a sulfide, and the other layer of the first layer and the second layer comprises a polymer.

2. The prosthetic valve of claim 1, wherein the one layer comprises a metal oxide.

3. The prosthetic valve of claim 2, the metal oxide comprising aluminum oxide ($Al_2O_3$).

4. The prosthetic valve of claim 1, wherein a density of the fibrous matrix is symmetric across a thickness of at least one of the plurality of leaflets.

5. The prosthetic valve of claim 1, wherein a density of the fibrous matrix is asymmetric across a thickness of at least one of the leaflets.

6. The prosthetic valve of claim 1, each leaflet having an upstream side and a downstream side, wherein a density of the fibrous matrix is greater on the upstream side of each leaflet than on the downstream side of each leaflet.

7. The prosthetic valve of claim 1, wherein a flexural stiffness of at least one of the leaflets is less than 8 g/cm.

8. The prosthetic valve of claim 1, the fibrous matrix comprising polymeric fibers having an average diameter of about 10 nanometers to about 10 micrometers.

9. The prosthetic valve of claim 1, further comprising a frame, wherein the leaflets are attached to the frame.

10. A prosthetic valve comprising:
a plurality of leaflets,
the leaflets each having a root portion and an edge portion substantially opposite the root portion and movable relative to the root portion to coapt with a respective edge portion of at least one of the other leaflets of the plurality of leaflets,
each leaflet among the plurality of leaflets comprising a fibrous matrix, the fibrous matrix comprising polymeric fibers; and
a coating surrounding individual polymeric fibers within the fibrous matrix, wherein the coating comprises a material selected from the group consisting of a metal oxide, a nitride, a carbide, or a sulfide;
wherein a flexural stiffness of the leaflets is less than 8 g/cm.

11. The prosthetic valve of claim 10, the coating comprising a metal oxide, the metal oxide comprising aluminum oxide ($Al_2O_3$).

12. The prosthetic valve of claim 10, wherein a density of the fibrous matrix is asymmetric across a thickness of the leaflets.

13. The prosthetic valve of claim 10, each leaflet having an upstream side and a downstream side, wherein a density of the fibrous matrix is greater on the upstream side of each leaflet than on the downstream side of each leaflet.

14. The prosthetic valve of claim 10, the fibrous matrix comprising polymeric fibers having an average diameter of about 10 nanometers to about 10 micrometers.

15. The prosthetic valve of claim 10, further comprising a frame, wherein the leaflets are attached to the frame.

16. A prosthetic valve comprising:
a plurality of leaflets,
the leaflets each having a root portion and an edge portion substantially opposite the root portion and movable relative to the root portion to coapt with a respective edge portion of at least one of the other leaflets of the plurality of leaflets,
the leaflets comprising a first zone and a second zone across a thickness thereof,
the first zone comprising a first fibrous matrix, the first fibrous matrix comprising polymeric fibers;
the second zone comprising a second fibrous matrix, the second fibrous matrix comprising polymeric fibers;
a coating surrounding individual polymeric fibers within the first fibrous matrix, the coating comprising a material selected from the group consisting of a metal oxide, a nitride, a carbide, or a sulfide.

17. The prosthetic valve of claim 16, the first zone having a different fiber density than the second zone.

18. The prosthetic valve of claim 16, wherein the first zone and the second zone have a combined thickness of 0.002" to 0.02".

19. The prosthetic valve of claim 16, the polymeric fibers of the first fibrous matrix comprising a polymer selected from the group consisting of poly(ethylene oxide), polyethylene, polyisobutylene polyurethane (PIBU), poly(styrene-block-isobutylene-block-styrene (SIBS), polypropylene, polystyrene, polyvinylchloride, polyisobutylene (PIB), poly(styrene) polyurethanes, polyvinylidene difluoride, poly(methyl methacrylate), polyethylene glycol, polyanilines, polypyrroles, polythiophenes, polyphenols, polyacetylenes, polyphenylenes, polyacrylonitriles, polylactic acids, polycaprolactone, polyglycolides, polyvinyl acetates, cellulose acetate, chitosan, proteins, carbohydrates and copolymers including one or more of these.

* * * * *